United States Patent [19]

Haber et al.

[11] Patent Number: 4,826,489
[45] Date of Patent: May 2, 1989

[54] DISPOSABLE SAFETY SYRINGE HAVING MEANS FOR RETRACTING ITS NEEDLE CANNULA INTO ITS MEDICATION CARTRIDGE

[75] Inventors: Terry M. Haber, Lake Forest; Clark B. Foster, El Toro; William H. Smedley, Lake Elsinore, all of Calif.

[73] Assignee: Habley Medical Technology Corporation, Laguna Hills, Calif.

[21] Appl. No.: 143,751

[22] Filed: Jan. 14, 1988

[51] Int. Cl.⁴ .............................................. A61M 5/32
[52] U.S. Cl. .................... 604/195; 604/198; 604/232
[58] Field of Search ............ 604/198, 197, 196, 195, 604/218, 228, 232, 263, 194, 193, 110

[56] References Cited

U.S. PATENT DOCUMENTS

| | | | |
|---|---|---|---|
| 2,722,215 | 11/1955 | Dahlgren | 604/228 X |
| 2,880,725 | 4/1959 | Kendall | 604/196 |
| 2,888,924 | 6/1959 | Dunmire | 604/196 |

*Primary Examiner*—John D. Yasko
*Attorney, Agent, or Firm*—Morland C. Fischer

[57] ABSTRACT

A disposable safety syringe, such as a dental syringe, comprising a syringe cylinder having proximal and distal ends, a pre-filled fluid medication cartridge movable through the cylinder, and a double-ended hypodermic needle cannula extending through and being bonded to a bore formed at the distal end of the cylinder. A piston is movable distally through the cartridge for expulsing the fluid contents via the needle cannula and for engaging one end of the cannula. The cartridge is moved through the cylinder and into contact with the distal end thereof to cause the distal end to be relocated relative to the needle cannula. Accordingly, the bond between the distal bore and the needle cannula is broken. The piston is then moved proximally through the medication cartridge for correspondingly relocating the needle cannula through the distal bore and into the empty medication cartridge, wherein the cannula is completely shielded and irretrievably located. The syringe is now rendered non-reuseable and suitable for a safe disposal without subjecting health care workers to an accidental needle strike as a consequence of a careless handling or cutting of the cannula.

33 Claims, 3 Drawing Sheets

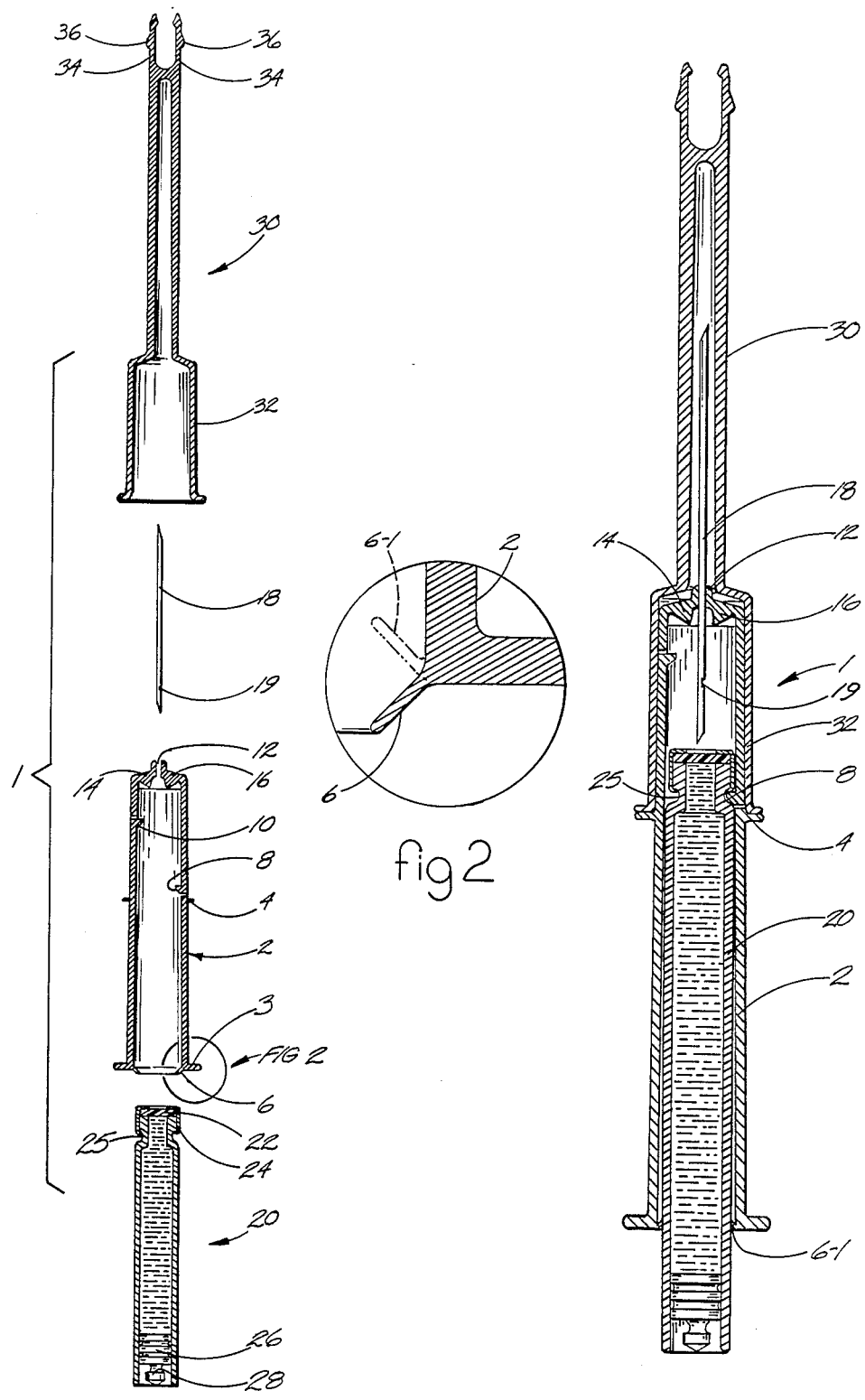

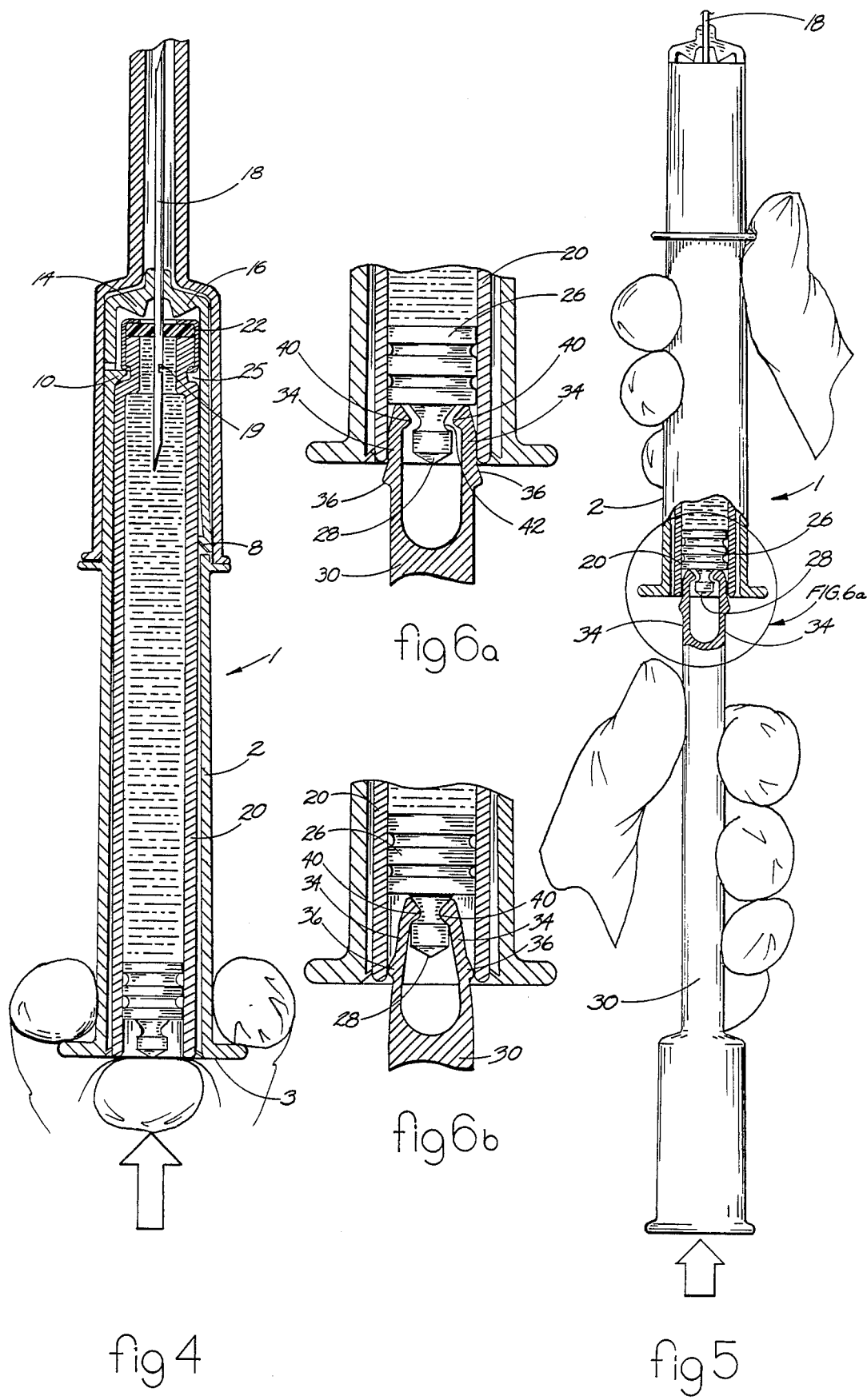

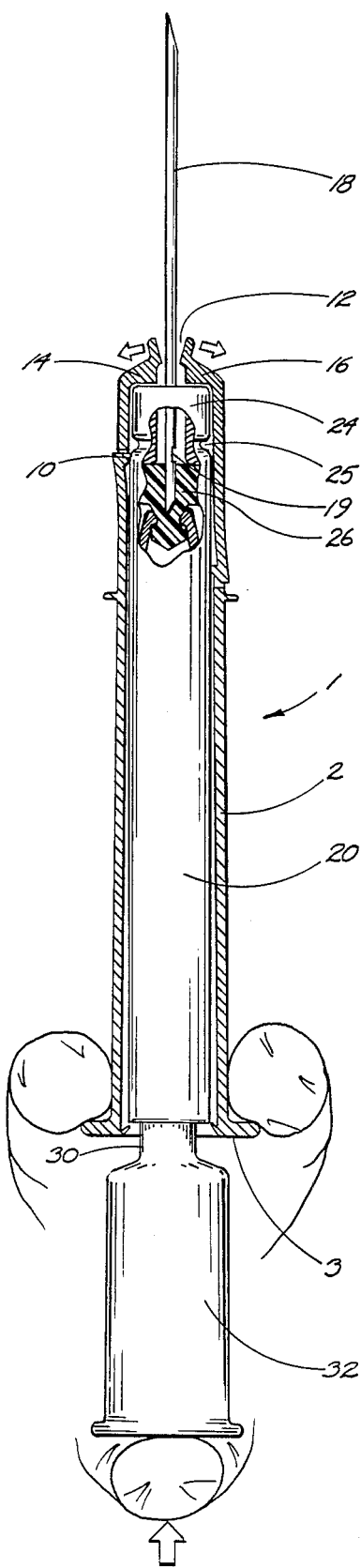
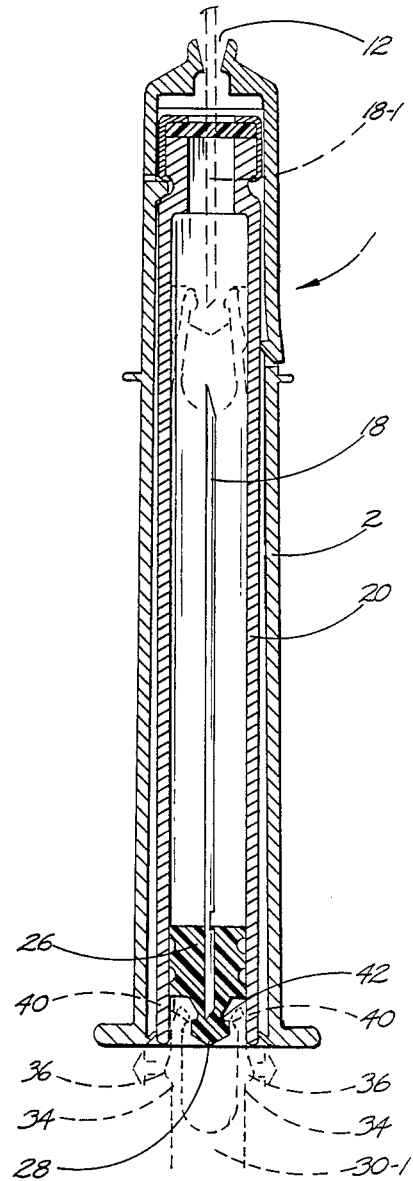
fig 7
fig 8

DISPOSABLE SAFETY SYRINGE HAVING MEANS FOR RETRACTING ITS NEEDLE CANNULA INTO ITS MEDICATION CARTRIDGE

BACKGROUND OF THE INVENTION

1. FIELD OF THE INVENTION

This invention relates to a disposable safety syringe, such as a dental syringe, having a pre-filled fluid medication cartridge and a double-ended hypodermic needle cannula, and, more particularly, to means by which the needle cannula may be relocated from an axially extended position, at which to inject the fluid contents of the medication cartridge into a targeted tissue area, to a retracted position, at which the cannula is withdrawn into and completely shielded by the medication cartridge at the interior of the syringe cylinder.

2. PRIOR ART

Dental syringes of the type having a pre-filled cartridge of fluid medication and a double-ended hypodermic needle are well-known in the art for injecting such medication from the cartridge to a targeted tissue area of a patient. However, at the completion of the injection, the needle is typically locked in an axially extended position projecting outwardly from a distal bore formed through the syringe cylinder.

In some cases, the syringe may be used to treat a patient having a communicable disease. Prior to disposing the syringe, the hypodermic needle is frequently broken or destroyed to prevent reuse. Dental office workers are especially susceptable to accidental and potentially infectious needle strikes due to the careless handling or breaking of the needle and disposing of the syringe after use. The resulting mini-accident caused by an accidental needle strike typically requires a blood test for such diseases as AIDS and hepatitis. The corresponding cost and ineffiency of testing dental office workers who have received such an accidental needle strike result in considerable waste, which may be particularly damaging to a dental facility which is striving for economy.

The following patent applications, which are assigned or will be assigned to the assignee of the present patent application, disclose syringes having a pre-filled medication cartridge and a needle which is retractable within the syringe cylinder:

Application Ser. No. 39,715 filed Apr. 20, 1987 and entitled "Dental syringe having an automatically retractable needle"; application Ser. No. 101,251 filed Sept. 25, 1987 and entitled "Disposable, presterilizable syringe for a pre-filled medication cartridge"; and Application Docket No. HMTC-34 entitled "Retractable needle syringe with integral spring".

SUMMARY OF THE INVENTION

Briefly, the present invention relates to a disposable safety syringe, such as a dental syringe, or the like, by which a hypodermic needle cannula may be retracted into an evacuated medication cartridge at the interior of the syringe cylinder so as to prevent reuse of the syringe and permit the syringe to be safely handled and discarded without subjecting health care workers to an accidental needle strike and the spread of a contagious and, possible life threatening, disease. The syringe includes a hollow cylinder having proximal and distal ends and a bore formed through the distal end. A pair of inwardly projecting needle retaining shoulders are hingedly connected to the distal end of the cylinder to define a bore therebetween. A double-ended needle cannula extends through and is retained within the distal bore by means of a thermal bond to prevent movement of the cannula relative to the bore. A first end of the cannula extends into the interior of the cylinder, and an opposite, second end of the cannula extends outwardly from the cylinder for administering an injection at a targeted tissue area.

A pre-filled fluid medication cartridge is loaded into the cylinder through the proximal end so as to be spaced axially from the first end of the needle cannula. The cartridge contains a piston which is movable through the cartridge to expulse the fluid contents. A combination needle sheath/piston stem has a relatively wide sleeve formed at one end and a pair of flexible gripping arms projecting axially from the opposite end. Initially, the wide sleeve of the needle sheath/piston stem surrounds and sheaths the second end of the needle cannula to prevent the contamination thereof and avoid an accidental needle strike.

In operation, the medication cartridge is advanced distally through the syringe cylinder until the first end of the needle cannula penetrates the cartridge to communicate with the fluid contents thereof. The second end of the cannula is unsheathed, and the flexible gripping arms of the needle sheath/piston stem are detachably connected to the piston at the interior of the medication cartridge to complete a piston assembly. An axial force is then applied to the piston stem to correspondingly drive the piston distally through the cartridge to expulse the contents thereof via the cannula, such that the piston is penetrated by the first end of the cannula. After the medication cartridge has been emptied, the axial force is reapplied to the piston stem to cause the cartridge to move distally through the syringe cylinder and into contact with the needle retaining shoulders at the distal end of the cylinder. The axial force is transferred from the cartridge to the distal end of the cylinder, whereby to cause the needle retaining shoulders to rotate relative to the needle cannula and thereby break the bond formed between the shoulders and the cannula. The distal bore is thereby opened to release the cannula therefrom. The piston stem then moves the piston proximally through the cartridge to correspondingly retract the cannula through the opened distal bore and into the medication cartridge, wherein the cannula is completely shielded and irretrievably located.

BRIEF DESCRIPTION OF THE DRAWINGS

FIG. 1 is an exploded view of the disposable safety syringe which forms the present invention;

FIG. 2 is an enlarged detail of the syringe of FIG. 1;

FIG. 3 is a cross-section showing the syringe of FIG. 1 in the assembled relationship;

FIG. 4 illustrates the operational step of moving a medication cartridge distally through the syringe cylinder until a needle cannula penetrates the cartridge at the interior of the syringe cylinder;

FIG. 5 illustrates the detachable connection of a piston stem to a piston of the medication cartridge by which the piston can be moved axially through the cartridge;

FIGS. 6a and 6b illustrate enlarged details for detachably connecting the piston stem to the piston of FIG. 5;

FIG. 7 illustrates the operational step of moving the medication cartridge distally through the syringe cylinder and into contact with the distal end of the cylinder for breaking the bond formed between the needle cannula and a distal bore; and FIG. 8 illustrates the operational step of moving the piston proximally through the medication cartridge for retracting the needle cannula through the distal bore and into said cartridge.

DESCRIPTION OF THE PREFERRED EMBODIMENTS

The disposable safety syringe 1 of the present invention is best described while referring to the drawings, where FIG. 1 illustrates an exploded view of the syringe components. More particularly, syringe 1 includes a hollow cylinder or barrel 2 having an open proximal end and a partially closed distal end. A major flange 3 extends around the open proximal end of the syringe cylinder 2. A relatively narrow flange 4 extends around the periphery of cylinder 2 intermediate the proximal and distal ends. An integral, flexible sealing gasket 6 projects outwardly through the open proximal end of cylinder 2. The details of gasket 6 will be described in greater detail hereinafter when referring to FIG. 2. Proximal and distal locking detents 8 and 10 project inwardly from opposite sides of the cylinder 2. The functions performed by locking detents 8 and 10 will be better described when referring to FIG. 3. Briefly, however, a notch (best illustrated in FIG. 3) is formed through cylinder 2 around the top and sides of locking detents 8 and 10 to permit detents 8 and 10 to rotate slightly in an outward direction relative to cylinder 2.

The distal end of cylinder 2 includes a narrow bore 12 which receives and retains a double-ended hypodermic needle cannula 18 to permit fluid to be delivered from the syringe 1 to a targeted tissue area of a patient. Needle cannula 18 includes a fluid port 19 (best shown in FIG. 3) which enables substantially all of the fluid from syringe 1 to be injected into the targeted tissue area. The distal bore 12 is defined by a pair of oppositely disposed needle retaining shoulders 14 and 16 which, as will soon be explained, are hingedly connected to the distal end of cylinder 2 so as to be adapted for rotation in an outward direction relative to the cylinder (best illustrated in FIG. 7).

A pre-filled medication cartridge or ampule 20 is of suitable size so as to be loaded into the syringe cylinder 2 through the open proximal end thereof so that the contents of cartridge 20 may be delivered to the targeted tissue area via needle cannula 18. Cartridge 20 is typically formed from a transparent material (e.g. glass, or the like) and is filled with a fluid medication, such as Novacaine, or the like. A rubber seal 22 extends across a distal end of cartridge 20, and a metal end cap 24 secures seal 22 to the cartridge. A neck 25 of relatively reduced diameter is formed around the periphery of cartridge 20 below end cap 24. A piston 26 is located at the proximal end of cartridge 20. Piston 26 is slideable axially through the cartridge to expulse the fluid contents thereof (via cannula 18). The piston 28 of cartridge 26 includes a proximally projecting plug member 28, the purpose and advantage of which will be described when referring to FIGS. 6a and 6b.

Syringe 1 also includes a combination needle sheath and piston stem 30. The combination needle sheath and piston stem 30 has a substantially hollow, elongated body with a relatively wide sleeve 32 formed at one end and a pair of oppositely disposed, flexible gripping arms 34 projecting from the opposite end. A small locating bump 36 projects outwardly from each gripping arm 34.

As is best shown in FIG. 3, the combination needle sheath/piston stem 30 functions as a needle sheath, such that sleeve 32 receives and surrounds one end of the needle cannula 18. As is best shown in FIG. 5, needle sheath/piston stem 30 also functions as a piston stem, such that the pair of gripping arms 34 are releasably connected to the piston 26 of medication cartridge 20 to form a piston assembly.

FIG. 2 shows an enlarged detail of the flexible sealing gasket 6 which is integrally connected to the proximal end of syringe cylinder 2. More particularly, gasket 6 is hingedly connected to cylinder 2 so as to be adapted for rotation from an outwardly projecting position (as illustrated in FIG. 1) to an inwardly projecting position relative to the interior of cylinder 2 (as shown in phantom and designated by the reference numeral 6-1 of FIG. 2). The means and advantage for rotating sealing gasket 6 into the interior of cylinder 2 is now described while referring to FIG. 3.

FIG. 3 shows the disposable safety syringe 1 in an assembled configuration so as to be suitable for packaging and shipment to health care workers. In the assembled relationship, the needle cannula 18 is retained within the distal bore 12 of syringe cylinder 2 by a thermal bond that is formed between the cannula and the opposing needle retaining shoulders 14 and 16. One end of cannula 18 extends proximally into the interior of cylinder 2 and is adapted to penetrate the seal of the medication cartridge 20. The opposite end of cannula 18 extends distally and outwardly from the cylinder 2 for injecting the contents of cartridge 20 into the targeted tissue area. The distally extending end of needle cannula 18 is initially surrounded and protected by the needle sheath 30 so as to preserve the sterility of cannula 18 and prevent an accidental needle strike. More particularly, the relatively wide sleeve 32 of needle sheath 30 is placed over the proximal end of cylinder 2 until a flanged end of sheath 30 engages the intermediate flange 4 of cylinder 2. It may be desirable to heat seal sleeve 32 to flange 4 to prevent a premature removal of needle sheath 30 from cylinder 2.

The medication cartridge 20 is loaded through the open proximal end of and advanced distally through the syringe cylinder 2 until the proximal locking detent 8 is received in a snap-fit engagement within the neck 25 of cartridge 20. Accordingly, cartridge 20 is initially retained within cylinder 2 in spaced, axial alignment with the needle cannula 18, such that a small portion of the cartridge 20 extends outwardly from the proximal end of cylinder 2.

At the same time that medication cartridge 20 is loaded into the syringe cylinder 2, the flexible sealing gasket 6 is engaged by cartridge 20 and rotated from the outwardly projecting position of FIG. 1 to the inwardly projecting position (represented by reference numeral 6-1) of FIG. 2. That is, the distal advancement of cartridge 20 through cylinder 2 automatically rotates gasket 6, so that an air-tight seal is formed between cylinder 2 and cartridge 20 to preserve the sterility of needle 18 by preventing contaminated air from reaching cannula 18 via the space between the cylinder 2 and the cartridge 20.

The operation of the syringe 1 of the present invention is now described while referring to FIGS. 4-8 of the drawings. In FIG. 4, the user places his index and middle fingers under the major flange 3 of syringe cylinder 2 and his thumb against the end of medication cartridge 20 which extends outwardly from the cylinder 2

(best represented in FIG. 2). The user then uses his thumb to exert an axial force upon the medication cartridge 20 (in the direction of the reference arrow) by which to rotate proximal locking detent 8 out of engagement with the neck 25 of cartridge 20 and thereby permit cartridge 20 to be driven distally through cylinder 2. The continued application of the axial force to cartridge 20 causes the cartridge to slide through cylinder 2 until the respective proximal ends of cartridge 20 and cylinder 2 lie adjacent one another and the proximally extending end of cannula 18 penetrates the rubber seal 22 to communicate with the fluid contents of cartridge 20, so that an injection of the contents may be subsequently administered. Accordingly, the distal locking detent 10 is received in a snap-fit engagement within the neck 25 of cartridge 20, and the cartridge 20 is retained in spaced proximity to the needle retaining shoulders 14 and 16 at the distal end of syringe cylinder 2.

In FIG. 5 of the drawings, the user removes the needle sheath/piston stem 30 to unsheath the distally extending end of needle cannula 18. The user then grasps the cylinder 2 of syringe 1 with one hand and uses his opposite hand to attach needle sheath/piston stem 30 to the piston 26 of medication cartridge 20 to complete a piston assembly comprising a piston head 26 and an elongated piston stem 30.

More particularly, and referring concurrently to FIGS. 5 and 6 of the drawings, the user applies an axial force (in the direction of the reference arrow in FIG. 5) to the piston stem 30 to move the flexible gripping arms 34 through the proximal end of medication cartridge 20 and adjacent the plug member 28 of piston 26. As is best shown in FIG. 6a, each gripping arm 34 terminates at an inwardly projecting retaining finger 40. As the piston stem 30 is moved through the cartridge 20 (in the manner illustrated in FIG. 6b) to drive the piston 26 distally through the cartridge, the locating bumps 36 of gripping arms 34 will contact the interior walls of cartridge 20, whereby to cause the flexible gripping arms 34 to rotate inwardly towards plug member 28. A rotation of the gripping arms 34 correspondingly causes the inwardly projecting retaining fingers 40 to be rotated into engagement with and releasably retained by a relatively narrow neck 42 formed around the plug member 28 of piston 26. Therefore, so long as the locating bumps 36 on gripping arms 34 of piston stem 30 are located within the interior of medication cartridge 20, the retaining fingers 40 will be held within the neck 42 of plug member 28 to prevent the detachment of piston stem 30 from piston 26.

In FIG. 7 of the drawings, the user administers an injection by keeping his index and middle fingers located behind the major flange 3 of cylinder 2 and relocating his thumb to the sleeve 32 of piston stem 30. The user then applies an axial force to sleeve 32 (in the direction of the reference arrow) to drive the piston 26 distally through medication cartridge 20 to expulse the fluid contents thereof through the needle cannula 18 and into the targeted tissue area of the patient. It may be noted that by virtue of the fluid port 19 in cannula 18, substantially all of the fluid may be expulsed from cartridge 20 as the piston 26 is advanced to the distal end of the cartridge. Moreover, the proximally extending end of the needle cannula 18 penetrates and is thereby connected to piston 26 when the piston is moved completely through cartridge 20 to expulse the fluid therefrom.

Once the medication cartridge 20 has been emptied and the injection completed, the user continues to apply an axial force to the sleeve 32 of piston stem 30. Accordingly, the piston 26 (which has already been driven to the distal end of cartridge 20) transfers the axially applied force to the cartridge, so as to cause the distal locking detent 8 to rotate out of engagement with the neck 25 of cartridge 20 and thereby permit an additional distal movement of the cartridge through the syringe cylinder 2. The continued application of the axially applied force to sleeve 32 advances medication cartridge 20 distally through cylinder 2 until the metal end cap 24 thereof is moved into contact with needle retaining shoulders 14 and 16. The axially applied force is then transferred from the cartridge 20 to the inwardly projecting needle retaining shoulders 14 and 16 to cause said shoulders to rotate (in the direction of the reference arrows) around their respective integral (i.e. living) hinges at the distal end of cylinder 2 to thereby break the thermal bond between needle cannula 18 and shoulders 14 and 16. With the bond broken and the needle 18 no longer retained between shoulders 14 and 16, the needle cannula 18 is free to move relative to shoulders 14 and 16 through the distal bore 12 of syringe cylinder 2.

To this end, FIG. 8 of the drawings shows the needle cannula 18 of syringe 1 being withdrawn through the distal bore 12 to be retracted within and completely surrounded by the empty medication cartridge 20. More particularly, the user grasps and pulls the piston stem 30 proximally through cylinder 2, whereby the needle is relocated from an axially extended position (shown in phantom and designated by reference numeral 18-1) to an inwardly retracted position. When the piston stem (shown in phantom and designated 30-1) is pulled to the proximal end of medication cartridge 20, such that the locating bumps 36 are removed therefrom, the retaining fingers 40 of the respective gripping arms 34 are automatically rotated (in the direction of the reference arrows) out of engagement with the neck 42 of piston plug member 28. Therefore, the piston stem 30 may be detached from piston 26 and discarded. However, the piston 26 remains disposed within the proximal end of cartridge 20, such that the needle 18 is retained at an inaccessible location within the interior of the cartridge. Accordingly, the syringe 1 is now suitable for disposal with the needle cannula 18 safely retracted within and completely shielded by both the medication cartridge 20 and the cylinder 2, whereby to prevent a reuse of the syringe 1 and its cannula 18 and avoid an accidental needle strike and the spread of a communicable and, possibly life threatening, disease by eliminating the need to handle or cut the cannula as has heretofore been required with conventional syringes.

It will be apparent that while a preferred embodiment has been shown and described, various modifications and changes may be made without departing from the true spirit and scope of the invention. For example, the syringe 1 of the present invention has been described as having application as a dental syringe. Nevertheless, this should not be regarded as a limitation of the scope of the invention, and the claims which are apppended hereto are applicable to other syringes which use a pre-filled medication cartridge, where it is desirable to retract the needle cannula within the cartridge in order to render the syringe safe for handling and/or disposal.

Having thus set forth a preferred embodiment of the invention, what is claimed is:

1. A syringe comprising:
    a hollow cylinder for containing a fluid having proximal and distal ends and a bore formed in said distal end;
    a needle cannula extending through and being retained by said distal bore, such that a first end of said cannula communicates with the interior of said cylinder and the second end of said cannula extends outwardly from said cylinder for injecting the fluid therefrom;
    means movable through said cylinder for forcing the fluid outwardly therefrom by way of said needle cannula;
    means by which to open said distal bore so as to release said needle cannula therefrom; and
    means by which to engage said needle cannula and to retract the second end of said cannula through said opened bore and into the interior of said cylinder.

2. The syringe recited in claim 1, further comprising a cartridge located within said cylinder and containing the fluid to be injected outwardly from said cylinder by way of said needle cannula.

3. The syringe recited in claim 2, wherein the means by which to open said distal bore so as to release said needle cannula is said cartridge, said cartridge being movable distally through said cylinder and into contact with the distal end thereof to relocate said distal end relative to said cannula.

4. The syringe recited in claim 3, wherein the distal end of said cylinder has at least one inwardly projecting shoulder, said cartridge being moved into contact with said shoulder at the interior of said cylinder, for rotating said distal end away from said needle cannula to thereby open said distal bore and release said cannula.

5. The syringe recited in claim 4, wherein the means by which to engage said needle cannula is a piston being movable distally through said cartridge for expulsing the fluid contents thereof and for receiving the first end of said cannula therewithin, said piston also being movable proximally through said cartridge to retract the second end of said cannula through said opened bore and into the cartridge.

6. The syringe recited in claim 2, wherein said cartridge is movable through said cylinder, said cylinder including first and second locking means spaced axially from one another for successively engaging said cartridge, said first locking means releasably engaging said cartridge at a relatively proximal position within said cylinder such that said cartridge is spaced axially from the first end of said needle cannula, and said second locking means releasably engaging said cartridge at a relatively distal position within said cylinder such that the first end of said cannula penetrates said cartridge and communicates with the fluid contents thereof.

7. The syringe recited in claim 2, wherein the means movable through said cylinder for forcing fluid outwardly therefrom is a piston movable through said cartridge for expulsing the fluid content of said cartridge, said cartridge being movable axially through said cylinder such that the first end of said needle cannula penetrates said cartridge to communicate with the fluid contents thereof.

8. The syringe recited in claim 7, wherein said needle cannula includes a fluid port located between the first and second ends of said cannula and disposed within said cartridge to receive fluid from said cartridge when said cannula penetrates said cartridge and said piston moves therethrough.

9. The syringe recited in claim 7, further comprising a piston stem to be detachably connected to said piston for moving said piston through said cartridge to expulse the fluid contents thereof.

10. The syringe recited in claim 9, wherein said piston stem includes a hollow sleeve formed at one end thereof, said sleeve surrounding and sheathing the second end of said needle cannula prior to the connection of said piston stem to said piston.

11. The syringe recited in claim 9, wherein said piston stem includes a pair of flexible gripping arms having respective raised surfaces projecting outwardly therefrom, said raised surfaces contacting the walls of said cartridge for urging said gripping arms toward said piston to be detachably connected thereto when said piston stem moves said piston through said cartridge.

12. The syringe recited in claim 11, wherein said piston includes a region of relatively narrow cross-section and the gripping arms of said piston stem include inwardly projecting retaining fingers, said retaining fingers being moved into said region of relatively narrow cross-section for detachably connecting said piston stem to said piston when said piston stem moves said piston through said cartridge.

13. A syringe comprising:
    a hollow cylinder having proximal and distal ends;
    a cartridge located within said cylinder and containing a supply of fluid;
    a needle cannula extending through said distal cylinder end, such that a first end of said cannula is adapted to penetrate said cartridge to communicate with the fluid contents thereof and a second end of said cannula extends outwardly from said cylinder for injecting the fluid of said cartridge; and
    means for retracting said cannula into said cartridge at the interior of said cylinder after fluid has been expulsed from said cartridge.

14. The syringe recited in claim 13, further comprising a piston assembly movable through said cartridge and including a piston stem and a piston, said piston stem driving said piston distally through said cartridge for expulsing the fluid contents thereof via said needle cannula.

15. The syringe recited in claim 14, wherein said piston stem is detachably connected to said piston.

16. The syringe recited in claim 15, wherein said piston stem includes a hollow sleeve formed at one end thereof, said sleeve surrounding and sheathing the second end of said needle cannula prior to the connection of said piston stem to said piston.

17. The syringe recited in claim 15, wherein said piston stem includes a pair of flexible gripping arms, each arm having a respective inwardly projecting retaining finger, and said piston includes an area of relatively narrow cross-section, said gripping arms being rotated towards said piston such that said retaining fingers are located within said area of narrow cross-section for detachably connecting said stem to said piston when said piston assembly moves through said cartridge.

18. The syringe recited in claim 14, wherein the means for retracting said needle cannula into said cartridge is said piston assembly, said piston engaging the first end of said cannula after said first end penetrates said cartridge and said piston is moved distally through said cartridge to expulse the contents thereof, said piston stem moving said piston proximally through said cartridge to thereby retract said needle cannula therewithin.

19. The syringe recited in claim 14, wherein said needle cannula is releasably retained within a distal bore formed through the distal end of said cylinder, said cannula being bonded to said bore.

20. The syringe recited in claim 19, wherein the distal end of said cylinder has at least one inwardly projecting shoulder, said syringe further comprising means by which to move said cartridge distally through said cylinder and into contact with said shoulder at the interior of said cylinder to relocate said distal cylinder end relative to said needle cannula and thereby open said distal bore to release said cannula to be retracted into said cartridge.

21. The syringe recited in claim 13, further comprising a flexible gasket projecting inwardly from the periphery of said cylinder and forming a seal between said cylinder and said cartridge located therewithin.

22. A syringe comprising:
a cylinder having proximal and distal ends and a bore formed through said distal end;
a needle cannula extending through said distal bore and being bonded thereto to prevent the movement of said cannula relative to said bore, a first end of said cannula communicating with the interior of said cylinder and the second end of said cannula extending outwardly from said cylinder;
a fluid filled cartridge located within said cylinder so as to be spaced axially from the first end of said cannula, said cartridge having a piston which is movable therethrough for expulsing the fluid of said cartridge;
means for moving said cartridge distally through said cylinder such that the first end of said cannula penetrates said cartridge;
means for breaking the bond between said needle cannula and said distal bore so that said cannula is movable relative to said bore; and
means for engaging the first end of said cannula and retracting said cannula through said bore and into the interior of said cartridge after the fluid has been expulsed therefrom.

23. The syringe recited in claim 22, further comprising first and second locking means spaced axially from one another along said cylinder, said first locking means releasably engaging said cartridge at a relatively proximal location within said cylinder so that said cartridge is spaced axially from said needle cannula, and said second locking means releasably engaging said cartridge at a relatively distal position within said cartridge when said cartridge is moved distally through said cylinder so that said cartridge is penetrated by said needle cannula.

24. The syringe recited in claim 22, wherein the means for breaking the bond between said needle cannula and said distal bore is said cartridge, said cartridge being moved distally through said cylinder and into contact with the distal end thereof to relocate said distal end relative to said cannula and thereby permit said cannula to be moved through said bore.

25. The syringe recited in claim 22, wherein the means for engaging the first end of said needle cannula and for retracting said cannula is the piston of said cartridge.

26. The syringe recited in claim 25, further comprising a piston stem detachably connected to said piston for moving said piston through said cartridge, said piston stem driving said piston distally through said cartridge for expulsing the fluid thereof and for engaging the first end of said needle cannula, said piston stem moving said piston proximally through said cartridge for retracting said cannula through said distal bore and into said cartridge.

27. A syringe comprising:
a hollow cylinder having proximal and distal ends and a bore formed through said distal end;
a needle cannula being received in and retained by said distal bore, such that a first end of said cannula is in fluid communication with the interior of said cylinder and the second end of said cannula extends outwardly from said cylinder to be located at a targeted tissue area of a patient; and
means by which to open said distal bore so as to release said needle cannula and permit the removal of said cannula therefrom.

28. The syringe recited in claim 27, further comprising means by which to engage said needle cannula and remove said cannula from said distal bore for relocation completely within said cylinder.

29. The syringe recited in claim 27, further comprising a piston movable distally through said cylinder for expulsing the contents thereof via said cannula, the continued distal movement of said piston through said cylinder relocating the distal end of said cylinder relative to said cannula to thereby open said distal bore.

30. The syringe recited in claim 27, further comprising a cartridge located within said cylinder and containing a fluid to be injected into the targeted tissue area of the patient by way of said needle cannula, said cartridge being movable distally through said cylinder and into contact with the distal end thereof to relocate said distal end relative to said cannula and thereby open said distal bore.

31. The syringe recited in claim 30, wherein the distal end of said cylinder includes a proximally and inwardly projecting member, said cartridge being moved distally through said cylinder and into contact with said inwardly projecting member for relocating the distal end of said cylinder relative to said cannula to thereby open said distal bore.

32. A syringe comprising:
a hollow cylinder having proximal and distal ends and adapted to receive a supply of fluid therewithin;
a hypodermic needle cannula being retained by and extending outwardly from the distal end of said cylinder so as to be positioned to communicate with the fluid supply to be received within said cylinder, whereby said fluid supply can be injected into a targeted tissue via said cannula; and
means for displacing the distal end of said cylinder relative to said cannula to cause said distal end to release its retention of said cannula and thereby permit said cannula to be removed from the distal end of said cylinder.

33. The syringe recited in claim 32, wherein said means for displacing includes means for rotating the distal end of said cylinder in a distal direction away from said needle cannula to cause said distal end to release its retention of said cannula.

* * * * *